(12) United States Patent
Mainini et al.

(10) Patent No.: US 9,186,091 B2
(45) Date of Patent: Nov. 17, 2015

(54) SYSTEMS AND METHODS OF ANALYZING STANCE OF ANIMALS

(75) Inventors: Christopher E. Mainini, Knoxville, TN (US); Greg Gillis, Escondido, CA (US); Anita White, Knoxville, TN (US); Darryl Millis, Knoxville, TN (US); Erica Shoults, Mission, KS (US); Jessica Morris, Knoxville, TN (US); Rick Seltzer, Knoxvillle, TN (US)

(73) Assignee: Litecure, LLC, Newark, DE (US)

( * ) Notice: Subject to any disclaimer, the term of this patent is extended or adjusted under 35 U.S.C. 154(b) by 473 days.

(21) Appl. No.: 13/546,790

(22) Filed: Jul. 11, 2012

(65) Prior Publication Data

US 2013/0018282 A1 Jan. 17, 2013

Related U.S. Application Data

(60) Provisional application No. 61/506,554, filed on Jul. 11, 2011.

(51) Int. Cl.
*A61B 5/103* (2006.01)
*A61B 5/11* (2006.01)
*A61B 5/00* (2006.01)

(52) U.S. Cl.
CPC .............. *A61B 5/1036* (2013.01); *A61B 5/11* (2013.01); *A61B 5/743* (2013.01); *A61B 2503/40* (2013.01); *A61B 2562/0247* (2013.01); *A61B 2562/046* (2013.01)

(58) Field of Classification Search
CPC ...... A61B 5/11; A61B 5/1116; A61B 5/1121; A61B 5/1036; A61B 5/743
USPC ............................ 600/587, 595; 382/110, 286
See application file for complete search history.

(56) References Cited

U.S. PATENT DOCUMENTS

| | | | |
|---|---|---|---|
| 4,195,643 A | 4/1980 | Pratt, Jr. | |
| 4,233,845 A | 11/1980 | Pratt, Jr. | |
| 5,138,550 A | 8/1992 | Abraham et al. | |
| 5,186,062 A | 2/1993 | Roost | |
| 5,476,103 A | 12/1995 | Nahsner | |
| 5,485,402 A | 1/1996 | Smith et al. | |
| 5,736,656 A | 4/1998 | Fullen et al. | |
| 5,979,067 A * | 11/1999 | Waters | ............................ 33/512 |
| 5,988,106 A * | 11/1999 | van den Berg | ............. 119/51.02 |
| 6,038,935 A | 3/2000 | Fullen et al. | |
| 6,301,964 B1 | 10/2001 | Fyfe et al. | |
| 6,347,603 B1 | 2/2002 | Felger | |

(Continued)

FOREIGN PATENT DOCUMENTS

| CA | 2511427 | 7/2004 |
|---|---|---|
| WO | WO2012027845 | 8/2012 |
| WO | WO2012114064 | 8/2012 |

*Primary Examiner* — Max Hindenburg
(74) *Attorney, Agent, or Firm* — Pitts & Lake, P.C.

(57) ABSTRACT

Systems and methods of analyzing the distribution of weight of animals, including a base member, a plurality of sensor regions connected to the base member to respectively receive feet of the animal when the animal is standing, each sensor region having a plurality of sensors to generate signals indicative of weight applied by each foot to a respective sensor region, at least a portion of the sensors being located between the base member and the sensor regions and spaced apart proximate perimeter portions of each sensor region, and a control unit to generate an output indicative of the weight applied by each foot to the respective sensor regions based on an aggregation of the generated signals.

26 Claims, 10 Drawing Sheets

(56) References Cited

U.S. PATENT DOCUMENTS

| | | |
|---|---|---|
| 6,505,522 B1 | 1/2003 | Wilssens |
| 6,513,381 B2 | 2/2003 | Fyfe et al. |
| 6,602,210 B2 * | 8/2003 | Savet .................... 600/595 |
| 6,699,207 B2 | 3/2004 | Tasch et al. |
| 6,852,086 B2 * | 2/2005 | Atlas et al. .................... 600/595 |
| 6,915,233 B2 | 7/2005 | Han et al. |
| 6,993,954 B1 | 2/2006 | George et al. |
| 7,125,386 B2 * | 10/2006 | Kasahara .................... 600/595 |
| 7,591,165 B2 | 9/2009 | Papakostas et al. |
| 7,601,126 B2 * | 10/2009 | Keegan et al. .................... 600/595 |
| 8,279,057 B2 * | 10/2012 | Hirose .................... 340/517 |
| 8,376,964 B2 * | 2/2013 | Park et al. .................... 600/587 |
| 8,382,687 B2 * | 2/2013 | Lepine et al. .................... 600/595 |
| 8,797,166 B2 * | 8/2014 | Triener .................... 340/573.1 |
| 2002/0010390 A1 | 1/2002 | Guice et al. |
| 2002/0037092 A1 | 3/2002 | Craig et al. |
| 2002/0046713 A1 | 4/2002 | Otto |
| 2002/0055691 A1 | 5/2002 | Tasch et al. |
| 2003/0135097 A1 | 7/2003 | Wiederhold |
| 2010/0023293 A1 | 1/2010 | Walthert |
| 2010/0076692 A1 | 3/2010 | Vock et al. |
| 2010/0175634 A1 | 7/2010 | Chang et al. |
| 2010/0211355 A1 | 8/2010 | Horst et al. |
| 2010/0228521 A1 | 9/2010 | Hamamoto |
| 2010/0228522 A1 | 9/2010 | Hamamoto |
| 2010/0299074 A1 | 11/2010 | Chang et al. |
| 2011/0061606 A1 | 3/2011 | Sevadjian et al. |
| 2011/0313705 A1 | 12/2011 | Esser et al. |
| 2012/0046901 A1 | 2/2012 | Green et al. |
| 2012/0059235 A1 | 3/2012 | Davies |
| 2012/0062732 A1 | 3/2012 | Marman et al. |
| 2012/0123256 A1 | 5/2012 | Razansky et al. |
| 2012/0198932 A1 | 8/2012 | Van Dijk et al. |

* cited by examiner

SYSTEMS AND METHODS OF ANALYZING STANCE OF ANIMALS

CROSS-REFERENCE TO RELATED APPLICATIONS

This application claims the benefit of U.S. Provisional Patent Application Ser. No. 61/506,554, filed on Jul. 11, 2011, the disclosure of which is incorporated herein in its entirety by reference.

FIELD OF INVENTIVE CONCEPT

The present general inventive concept relates to analyzing the stance of animals, and more particularly, relates to systems and methods of detecting, diagnosing, and treating ailments in the stance of animals, such as dogs, cats, or other animals.

BACKGROUND

It is often desirable to analyze the stance of four legged animals such as dogs in order to detect and treat problems of stability and/or lameness caused by paw, leg, or other ailments. Attempts have been made in the field of veterinary medicine to measure the forces and timing of forces applied to the legs or hoofs of four-legged animals such as horses and other animals. This type of information is not only helpful for determining the stress applied to a hoof, but may also be used as a diagnostic tool to analyze gait, stride, lameness and other symptoms which occur as a result of an animal's natural motion. Furthermore, this data can be especially useful in the treatment of animals in order to prevent the development of undesirable ambulatory mechanics if the hoof or leg injuries are left undetected and untreated.

BRIEF SUMMARY

Embodiments of the present general inventive concept can be achieved by providing stance analyzer systems and methods to detect, diagnose, and treat ailments in the stance of animals, and to aid and/or train veterinarians and pet owners to diagnose ailments in the stance of a variety of animals, such as dogs, and to monitor pet therapy results in the treatment of such ailments.

Additional features and embodiments of the present general inventive concept will be set forth in part in the description which follows and, in part, will be obvious from the description, or may be learned by practice of the present general inventive concept.

Example embodiments of the present general inventive concept can also be achieved by providing a system to analyze the distribution of weight of an animal, including a base member, a plurality of sensor regions connected to the base member to respectively receive feet of the animal when the animal is standing, each sensor region having a plurality of sensors to generate signals indicative of weight applied by each foot to a respective sensor region, at least a portion of the sensors being located between the base member and the sensor regions and spaced apart proximate perimeter portions of each sensor region, and a control unit to generate an output indicative of the weight applied by each foot to the respective sensor regions based on an aggregation of the generated signals.

The control unit can collect the signals from each sensor region over time, and the output can include a stabilization signal to indicate when the weight applied by each foot is substantially constant over a period of time, based on a comparison of the collected signals. The control unit can include an input unit for a user to periodically start and/or stop the collection of data, and the control unit can automatically start and/or stop the collection of data based on a state of the stabilization signal.

The output can include a lameness signal to indicate lameness of the animal when the weight applied by at least one foot is a predetermined fraction of the weight applied by at least one other foot, and the output can include a distribution signal to indicate convergence and/or divergence of the weight applied by at least two different feet over time.

The system can include a food source holder to hold a food source proximate the animal's mouth when the animal is standing on the base member.

The system can include a fence member to stabilize the animal when the animal is standing on the base member.

The sensor regions are constructed such that the position of the animal's feet relative to each respective sensor region does not substantially change the generated signals.

The system can include a gimbal system to adjust a position and/or level of the base member to encourage the animal to expose a lame weight distribution.

The plurality of sensor regions can be respectively defined by one or more corresponding pressure plates having a first surface to receive the animal's feet and a second surface opposite the first surface and facing the base member to contact the plurality of sensors, the pressure plates being substantially rectangularly shaped such that the at least a portion of the sensors are located proximate four corners of the pressure plates.

Example embodiments of the present general inventive concept can also be achieved by providing a method of analyzing the distribution of weight of an animal, including providing a base member having a plurality of sensor regions on which the animal stands, locating each foot of the animal on a respective sensor region, generating signals indicative of weight applied by each foot to the respective sensor regions from a plurality of sensors, wherein at least a portion of the sensors are located between the base member and the sensor regions and are spaced apart proximate perimeter portions of each sensor region, and generating an output signal indicative of the weight applied by each foot to the respective sensor regions based on an aggregation of the generated signals.

The method can include periodically starting and/or stopping collection of data, based on a state of the stabilization signal.

The method can include adjusting a position and/or level of the base member while the animal is standing on the base member to expose a lame condition of the animal.

The method can include feeding the animal while the animal's feet are located on the respective sensor regions.

BRIEF DESCRIPTION OF THE FIGURES

The illustrated embodiments are representative of example techniques and structures to carry out the objects of the present general inventive concept, but the present general inventive concept is not limited to these illustrated embodiments. In the accompanying drawings, the sizes and relative sizes, shapes, and qualities of lines, entities, and regions may be exaggerated for clarity. A wide variety of additional embodiments will be more readily understood and appreciated through the following detailed description of the exemplary embodiments, with reference to the accompanying drawings in which.

DETAILED DESCRIPTION

Reference will now be made to the example embodiments of the present general inventive concept, examples of which are illustrated in the accompanying drawings and illustrations. The example embodiments are described herein in order to explain the present general inventive concept by referring to the figures.

Figure 1:
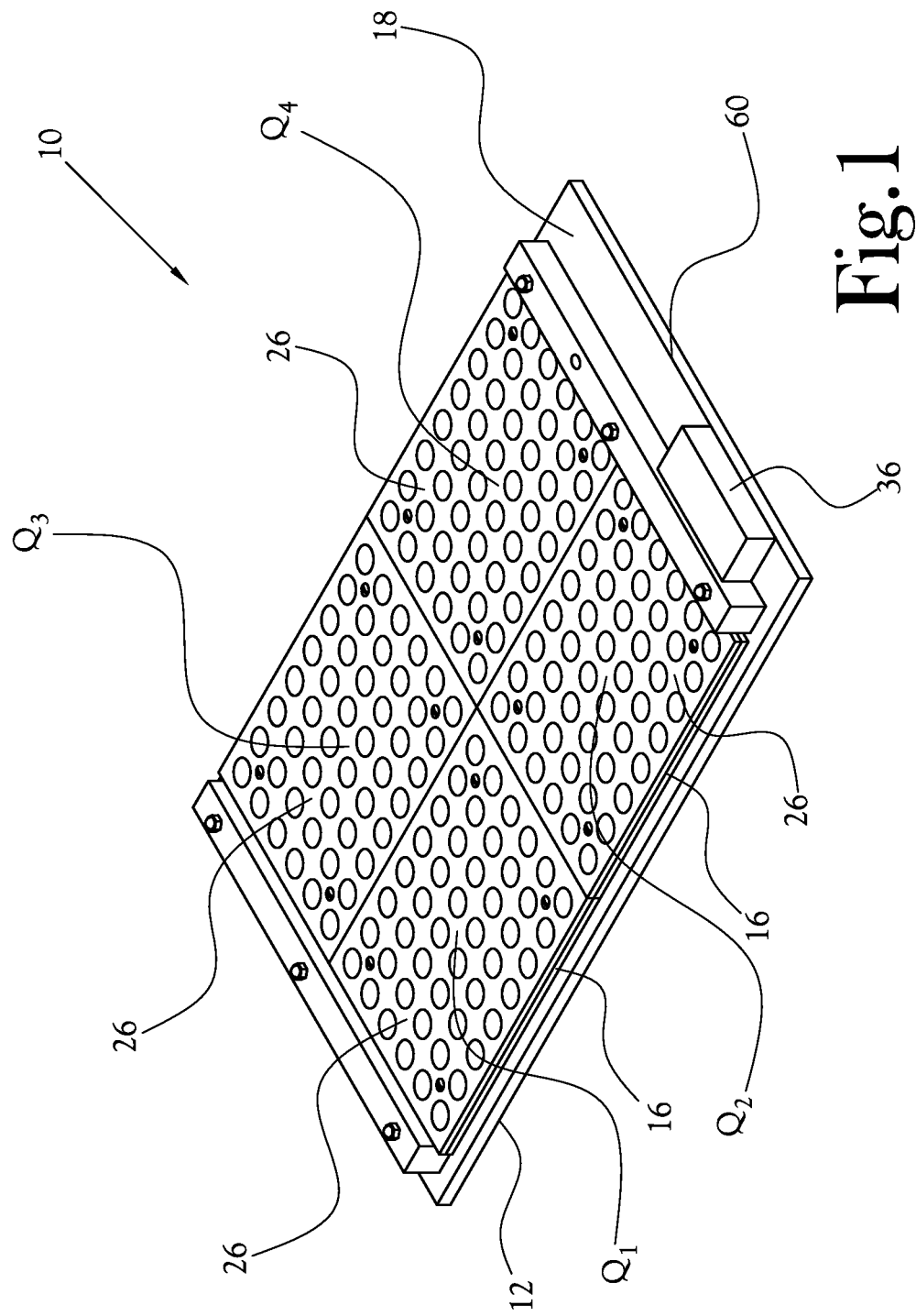
FIG. 1 is a perspective view illustrating a stance analyzer according to an example embodiment of the present general inventive concept.

FIG. 1 is a perspective view illustrating a stance analyzer system according to an example embodiment of the present general inventive concept. As illustrated in FIG. 1, the example stance analyzer 10 includes a base member 12 which defines a generally rectangular platform surface 18 sized and shaped to accommodate an animal standing thereon. In the illustrated embodiment, the base portion platform surface 18 is divided into four (4) quadrants Q1 to Q4, or sensor regions, each configured to receive one of the animal's legs. As used herein, the term "animal" may refer to any type of animal, such as for example a dog, cat, horse, livestock, or other type of animal. However, the present general inventive concept is not limited to use in connection with any particular type of animal. As will be discussed further hereinbelow, each quadrant Q1 to Q4 is configured to sense pressure characteristics exerted on the respective quadrant by a corresponding leg of the animal, such that the stance analyzer can diagnose lameness in animals, and can track healing and therapy progress from therapy to therapy.

Figure 2:
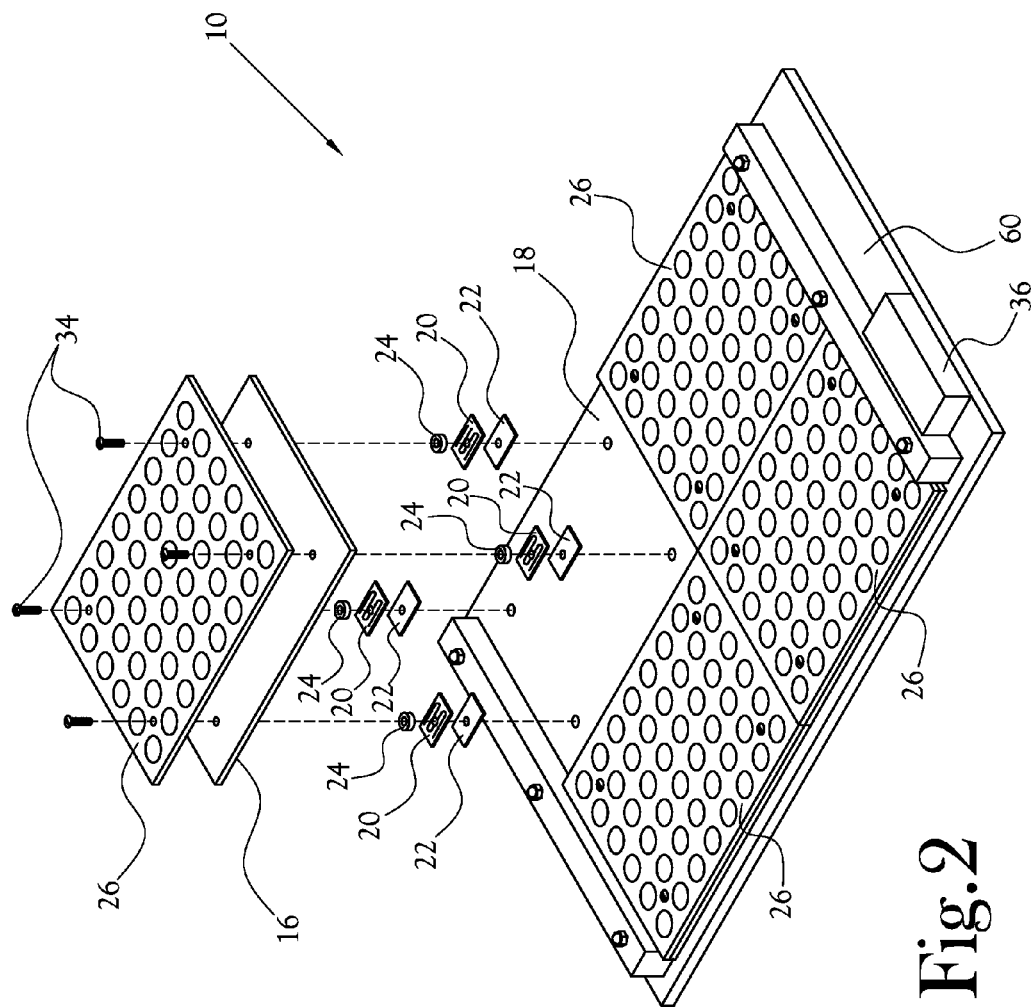
FIG. 2 is a partially-exploded view of the stance analyzer of FIG. 1.

Referring to FIGS. 1 and 2, the illustrated embodiments include a plurality of pressure plates 16 arranged in a substantially coplanar configuration, with each pressure plate 16 being disposed on at least a portion of each quadrant Q1 to Q4 of the platform surface 18. In the illustrated embodiment, each pressure plate 16 is sized to substantially cover its respective quadrant Q1 to Q4, such that the pressure plates 16 abut one another in an end-to-end and side-to-side fashion and cooperate to substantially cover the platform surface 18. However, it will be understood that such end-to-end relationship of the pressure plates 16 and substantial covering of the platform surface 18 by the pressure plates 16 is not necessary to accomplish the present general inventive concept. For example, it is possible for each pressure plate 16 to be spaced apart from an adjacent pressure plate 16 along the substantially coplanar configuration of the pressure plates 16, such that each pressure plate 16 covers a portion of its corresponding quadrant Q1 to Q4, but the present general inventive concept is not limited to such configuration. It is possible that multiple pressure plates can be used in conjunction with a particular quadrant, allowing the operator to selectively choose a corresponding pressure plates from each quadrant, depending, for example, on the shape and size of the animal's stance.

As illustrated in FIG. 2, a plurality of pressure transducers 20 are interposed between each pressure plate 16 and its respective quadrant Q1 to Q4 of the platform surface 18, with each pressure transducer 20 being configured to produce an output in response to changes in pressure exerted by one of the animal's legs on the pressure plates 16. In the illustrated embodiment, a first spacer 22 is provided beneath each pressure transducer 20 to separate each pressure transducer 20 slightly from the platform surface 18 and to provide a bearing surface for the pressure transducer 20 against the platform surface 18. A second spacer 24 is provided above each pressure transducer 20 to separate each pressure transducer slightly from its respective pressure plate 16 and to provide a bearing surface for each pressure plate 16 to bear against the corresponding pressure transducer 20. In this configuration, force resulting from a change in pressure exerted onto any portion of the pressure plates 16 is brought to bear against a pressure transducer 20 corresponding to the pressure plate 16 upon which the pressure is changed, such that the pressure transducer 20 may sense the change in pressure exerted onto a corresponding portion of the pressure plate 16.

In some embodiments, suitable fasteners may be provided in accordance with sound engineering judgment to secure the various pressure transducers 20 and associated first and second spacers 22, 24 between each pressure plate 16 and its respective quadrant Q1 to Q4 of the platform surface 18. For example, in the illustrated embodiment, a plurality of screw fasteners 34 are provided, with a screw fastener 34 being received through appropriate openings in each of the pressure plates 16, in associated pressure transducer 20 and first and second spacers 22, 24, and in corresponding locations in the platform surface 18, to secure the pressure transducer 20 and associated first and second spacers 22, 24 in position between each pressure plate 16 and its respective quadrant Q1 to Q4 of the platform surface 18. Other suitable fasteners will be readily apparent to one of ordinary skill in the art, and such fasteners may be used without departing from the spirit and scope of the present general inventive concept.

In the implementation of example embodiments of the present general inventive concept, each pressure plate 16 corresponding to one of the quadrants Q1 to Q4 is adapted to receive a respective foot of an animal standing thereon. Accordingly, when an animal stands upon the stance analyzer 10 with one leg standing on each pressure plate 16, pressure exerted onto each pressure plate 16 by the animal is detected and quantified by the various pressure transducers 20. Each second spacer 24 can be fabricated from a vibration-dampening material, such as, for example, but not limited to, neoprene, rubber, polymer material, or other suitable vibration-dampening material, such that the second spacers 24 cooperate to limit transfer of vibrations exerted onto, or by, the pressure plates 16 to the pressure transducers 20. In this or similar ways the second spacers 24 can limit fluctuation in pressure applied to the pressure transducers 20, thereby resulting in more constant pressures applied to the pressure transducers 20 by the pressure plates 16, with the result being that the pressure transducers 20 may produce more constant readings of pressure applied thereto. Using such a configuration has an advantage that the position of an animal's foot relative to a respective pressure plate will not substantially affect a corresponding signal generated by the pressure transducer.

In some embodiments, at least one mat 26 is provided along a top surface of the pressure plates 16. The mat 26 can be constructed from a vibration-dampening material, such that the mat 26 further assists in limiting transfer of vibrations exerted by the animal onto the pressure plates 16, and the mat 26 may provide a wear-resistant and/or more comfortable surface on which the animal may stand, although the mat is not limited to any particular type of material. Furthermore, it will be understood that, while certain advantages of the mat 26 will be recognized by one of skill in the art, inclusion of the mat 26 is not necessary to accomplish the objects of the present general inventive concept.

Referring to FIG. 2, a plurality of pressure transducers 20 and associated first and second spacers 22, 24 can be provided at spaced apart locations along each pressure plate 16 between the pressure plate 16 and its respective quadrant Q1 to Q4 of the platform surface 18. For example, in the illustrated embodiment of FIGS. 1 and 2, one pressure transducer 20 with associated first and second spacers 22, 24 is provided at each corner of each pressure plate 16. In this configuration, the various pressure transducers 20 of each pressure plate 16 may be used cooperatively to detect and analyze various characteristics of the stance of the animal positioned on the stance analyzer 10. For example, in some embodiments, readings of the various pressure transducers 20 beneath a single pressure plate 16 may be aggregated and compared to determine whether uneven or unbalanced pressure is being applied by an animal's leg to the pressure plate 16, which may be used, for example, as an indication that the animal may be leaning to one side or the other, and/or that the animal's foot is not positioned at a central location of the pressure plate 16, as may occur if the animal's stance is narrower or wider than the spacing of the central locations of the pressure plates 16 along the stance analyzer 10. For example, suppose the animal's feet are located off-center from each pressure plate 16 during operation. Here, if the signals from each transducer are aggregated and summed, the total weight applied to the pressure plate can still be calculated, even though the signals from each sensor may be different due to the uneven pressure being applied to the four corners of the pressure plate, since each sensor will be measuring its corresponding load, and all sensors in sum will aggregately measure the total load. Moreover, locating the sensors (e.g., transducers) proximate, or adjacent to, a perimeter portion of the plates (such as a corner) will enable the sensors to accurately measure movement of the plate, without possible tilting, or see-saw action of the plate with respect to a sensor which may occur if the sensor is located substantially inwardly of a perimeter portion of the plate. It is also possible to implement a calibration process before each use, wherein the sensors are zeroed-out to compensate for changing atmospheric conditions which may impact the readings of the transducers in different operating environments.

Those skilled in the art will recognize other types of data and analyses can be achieved using the various signals of the pressure transducers 20 provided along each pressure plate 16, and such data analyses may be performed without departing from the spirit and scope of the present general inventive concept. Furthermore, it will be recognized that additional components and/or devices may be included in the stance analyzer 10 to provide indications as to weight distribution characteristics of an animal standing on the platform surface 18. For example, the stance analyzer can include a gimbal system connected to the base member 12 to adjust the position and/or level of the platform surface 18 to exaggerate the animal's reaction to stance distribution characteristics to help expose a lame condition of the animal, while the animal is standing on the base member platform.

In some embodiments, the pressure transducers 20 can be an embodied as electronic strain gauges capable of generating an electric signal indicative of a weight applied to its respective pressure plate 16, such that in operation of the stance analyzer 10, electronic signals are produced by each strain gauge 20 in response to change in pressure applied thereto. It will be understood that the present general inventive concept is not limited to any particular type of transducer, and a variety of different pressure transducers, for example a semiconductor-based pressure transducer, can be implemented, using sound engineering judgment, to generate a weight measurement signal for each quadrant Q1 to Q4 corresponding to each foot, or leg, of the animal.

As illustrated in FIGS. 1 and 2, a housing 36 is provided along the base member 12 which can contain therein an appropriate power source to supply electrical power to each of the electronic strain gauges 20, but a variety of known power sources and/or circuit configurations can be provided to enable the pressure transducers 20 to receive operating power and to communicate output signals to an appropriate display device, control module, and/or analysis device.

Figure 3:
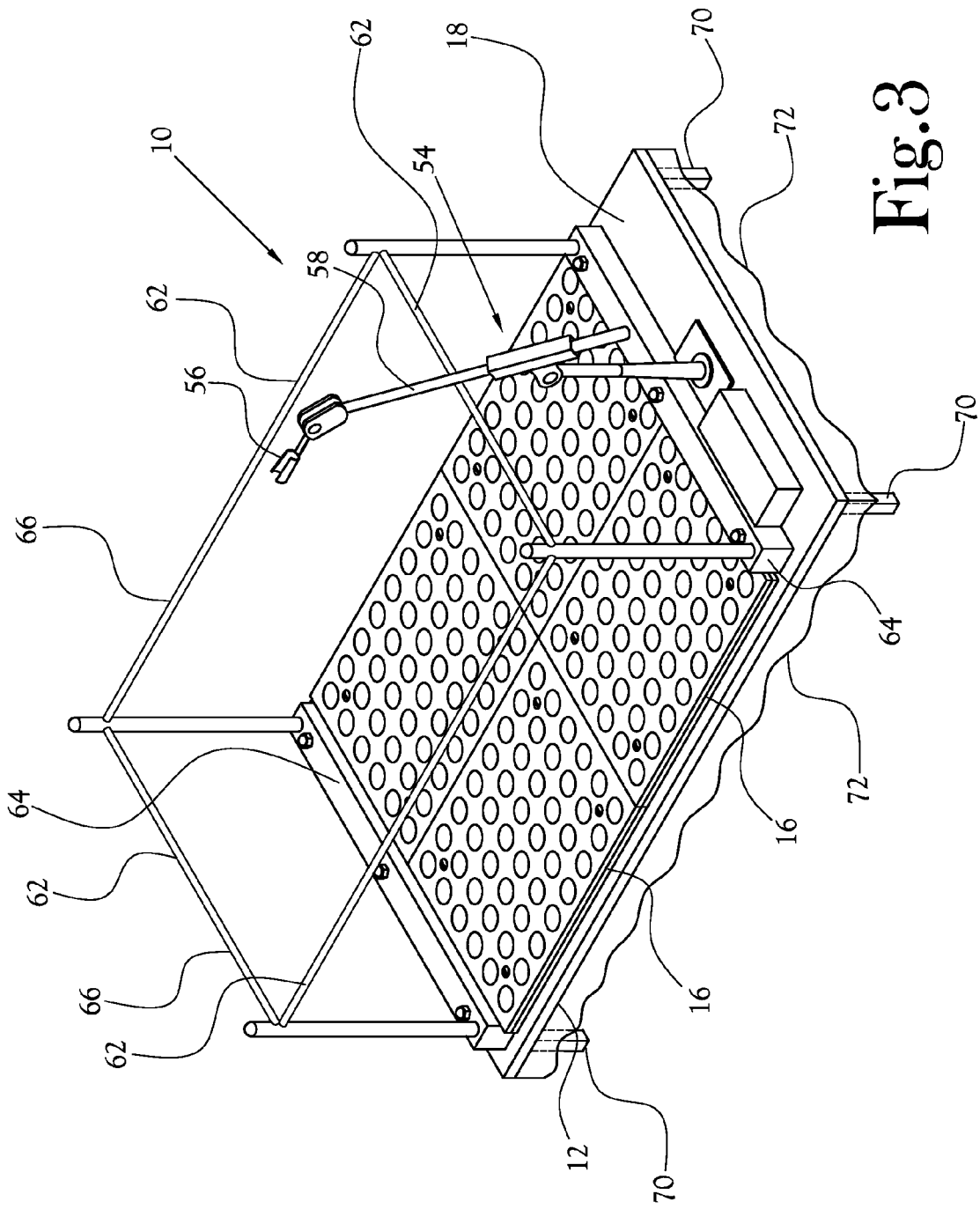
FIG. 3 is a perspective view illustrating a stance analyzer according to another example embodiment of the present general inventive concept.

Referring to FIG. 3, some embodiments include a food holder 54 for holding a food source to help stabilize the animal's stance on the platform. The food holder 54 can be provided proximate a forward end 60 of the stance analyzer 10 in order to assist in positioning and stabilizing an animal on the stance analyzer 10. Although the food holder is optional, it has been found that the animal focuses on and engages the food source while maintaining each leg on a respective pressure plate 16 (i.e., quadrant Q1 to Q4) of the base member 12, and thus remains more stable during data collection, improving efficiency of the system. In the illustrated embodiment, the food holder 54 includes a carriage 56 for carrying a food source and a boom 58 which is configured to position the carriage 56 and associated food source proximate the animal's mouth when the animal is situated on the stance analyzer 10 with each leg on a respective pressure plate 16. In the illustrated embodiment, the boom 58 is defined by a plurality of elongated members adjustably secured to one another and to the carriage 56 such that the boom 58 may be selectively reconfigured to reposition the carriage 56 at various heights and distances from the forward end 60 of the stance analyzer 10. However, it will be understood that the boom 58 may be constructed from any number of materials and in various configurations such that the boom 58 may position the carriage 56 as desired without departing from the spirit and scope of the present general inventive concept. The carriage 56 may be defined by any number of container and/or fastener devices, i.e., clips, straps, baskets, trays, etc., configured to hold a food source proximate the animal's head in such a manner as to entice the animal to engage the food source while the animal is standing on the base member.

Using a food source in conjunction with the system to feed the animal during operation assists the animal to focus on the food source during analysis, allowing the animal's head and body to remain relatively stable during data collection. Such stability of the animal's head in engagement with the food source has been found to encourage the animal to remain relatively still while positioned on the stance analyzer 10, thus improving quality and efficiency of data capture. It will be understood that the food source can be any of a variety of food or food-like products which a particular animal may find enticing, such as for example food, drink, flavored lickable animal treats such as the product sold by Radio Systems Corporation under the trademark "Lickety Stik®," scented objects, etc.

As illustrated in FIG. 3, to help stabilize the animal on the base member, the stance analyzer 10 can include a fence member. In this embodiment, the fence member includes a plurality of fence panels 62 connected to a plurality of support members 64 positioned at locations about a perimeter of the base member 12. The fence panels 62 cooperate to at least partially surround and enclose the quadrants Q1 to Q4 of the platform surface 18, thereby assisting in retaining an animal in a desired position on the pressure plates 16. In the illustrated embodiment, each fence panel 62 includes a substantially rigid cross-frame member 66, although it will recognized by one of ordinary skill in the art that numerous other configurations may be used to accomplish the fence member without departing from the present general inventive concept.

In certain embodiments, such as the embodiment illustrated in FIG. 3, the base 12 includes a plurality of legs 70 which are configured to carry and support the platform surface 18 in an elevated position above a support surface, such as the floor. In the embodiment of FIG. 3, a flexible skirt and/or gimbal system, generally represented by reference number 72, can be provided about a perimeter of the platform surface 18 and can be connected to the base member 12 to extend a bottom of the base member with respect to a plane defined by a lower extremity of the legs 70. In operation, the gimbal system includes adjustments (not illustrated) to adjust a position and/or level of the base member including a plurality of degrees of freedom. Adjusting the plane of the platform to a non-horizontal condition can encourage the animal to expose a lame condition that otherwise may be compensated by the animal's stance.

Figure 4:
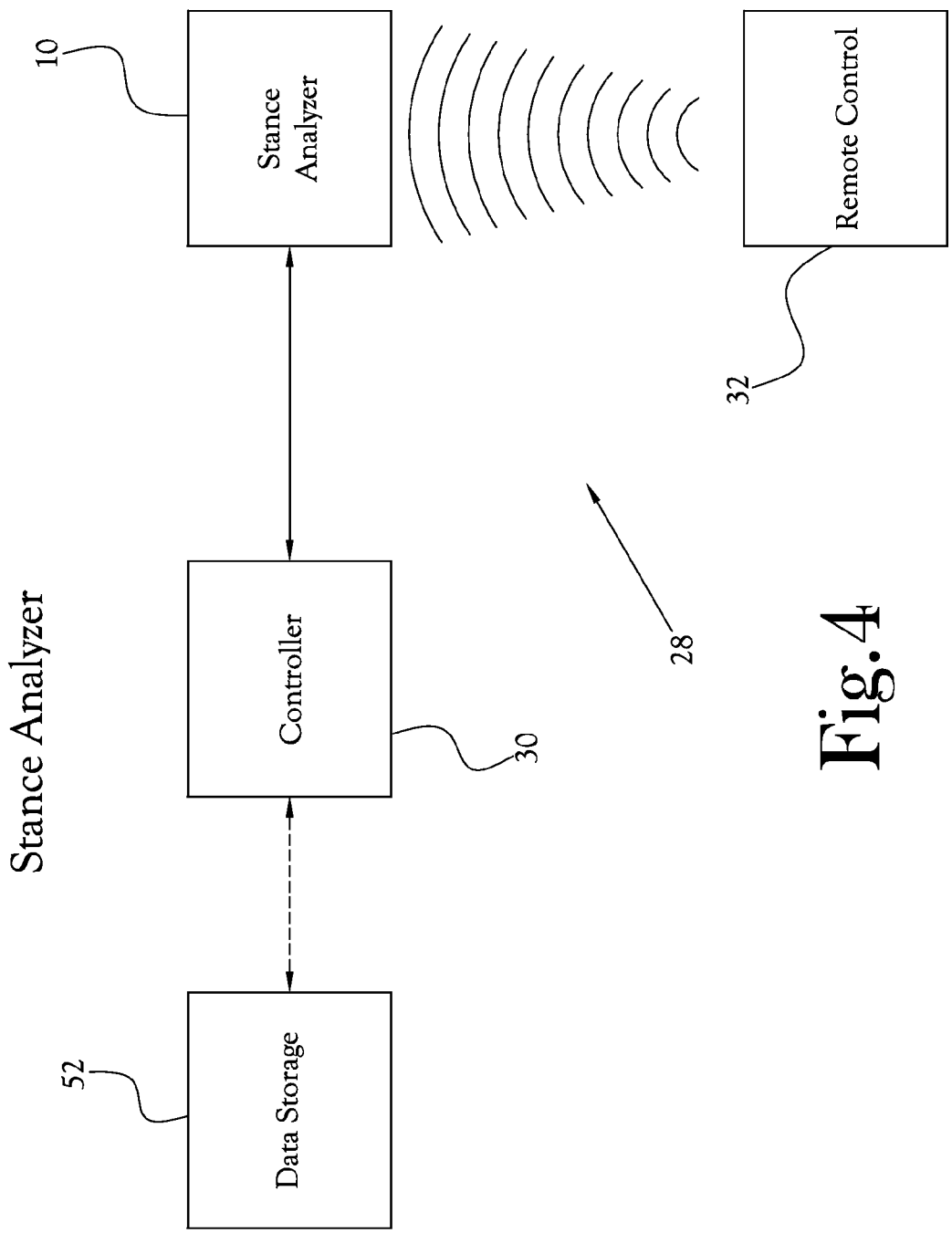
FIG. 4 is a block diagram illustrating a stance analyzer system according to an example embodiment of the present general inventive concept.

FIG. 4 is a block diagram illustrating a stance analyzer system 28 according to an example embodiment of the present general inventive concept. As illustrated in FIG. 4, the system 28 includes a stance analyzer 10 which is in communication with a control unit, or controller 30, and an optional remote control unit 32. The controller 30 may be a PC or other processing device. It will be recognized that, while the controller 30 (i.e., control module) and the remote control module 32 are illustrated as separate components, it is possible to provide the modules as a combined unit, as separate modules, or as an integrated unit with the stance analyzer 10 device. The controller can include a data link to process the collected data for transmission over a network to a remote user, for example transmission over the internet. In the illustrated embodiment, outputs of the various pressure transducers 20 of the stance analyzer 10 are in communication with the control module 30 through appropriate electrical connections, and the stance analyzer 10 can be in wireless communication with the remote control module 32, and/or the control module can be controlled by user controls at the control module, to control data collection options of the stance analyzer. The present general inventive concept is not limited to any particular type of communication protocol or control configuration, wired or wireless. To this extent, it is noted that the simplified diagrams and drawings referenced herein do not illustrate all of the various connections and assemblies of the various components to carry out the communication controls, however, those skilled in the art will understand how to implement such connections and assemblies, based on the illustrated components, figures, and descriptions provided herein, using sound engineering judgment. For example, in some embodiments, the control module 30 can include a data storage device 52 to collect signals from the various pressure transducers 20 of the stance analyzer 10, and a processor to process the signals to generate analyses data.

In operation, example embodiments of the stance analyzer system 28 can be used by veterinarians and/or pet owners to objectively diagnose lameness in four legged animals, and to further determine which legs are affected. When an animal stands with each foot, or paw, on a separate pressure plate 16, the weight distribution of the animal on each leg, or foot, can be determined and quantified. Data collected from the pressure transducers 20 of the stance analyzer 10 can be communicated to the control module 30, which may in turn communicate the data for recordation in the data storage unit 52 for subsequent access and analysis by the control module 30. The control module 30 can be programmed to analyze the various data outputs of the pressure transducers to calculate certain body weight distribution characteristics of the animal and to convert that information into selected displays and vectors providing ready data for understanding and tracking corrective treatment of the animal. Referring to FIG. 4, such analysis of the information can, in some embodiments, be accessed by a technician by means of the remote control module 32. The control module 30 can, in some embodiments, be programmed to include a graphic interface to generate visual representations of the detection, analysis, and/or diagnoses of the animal's stance and stability.

Figure 5:
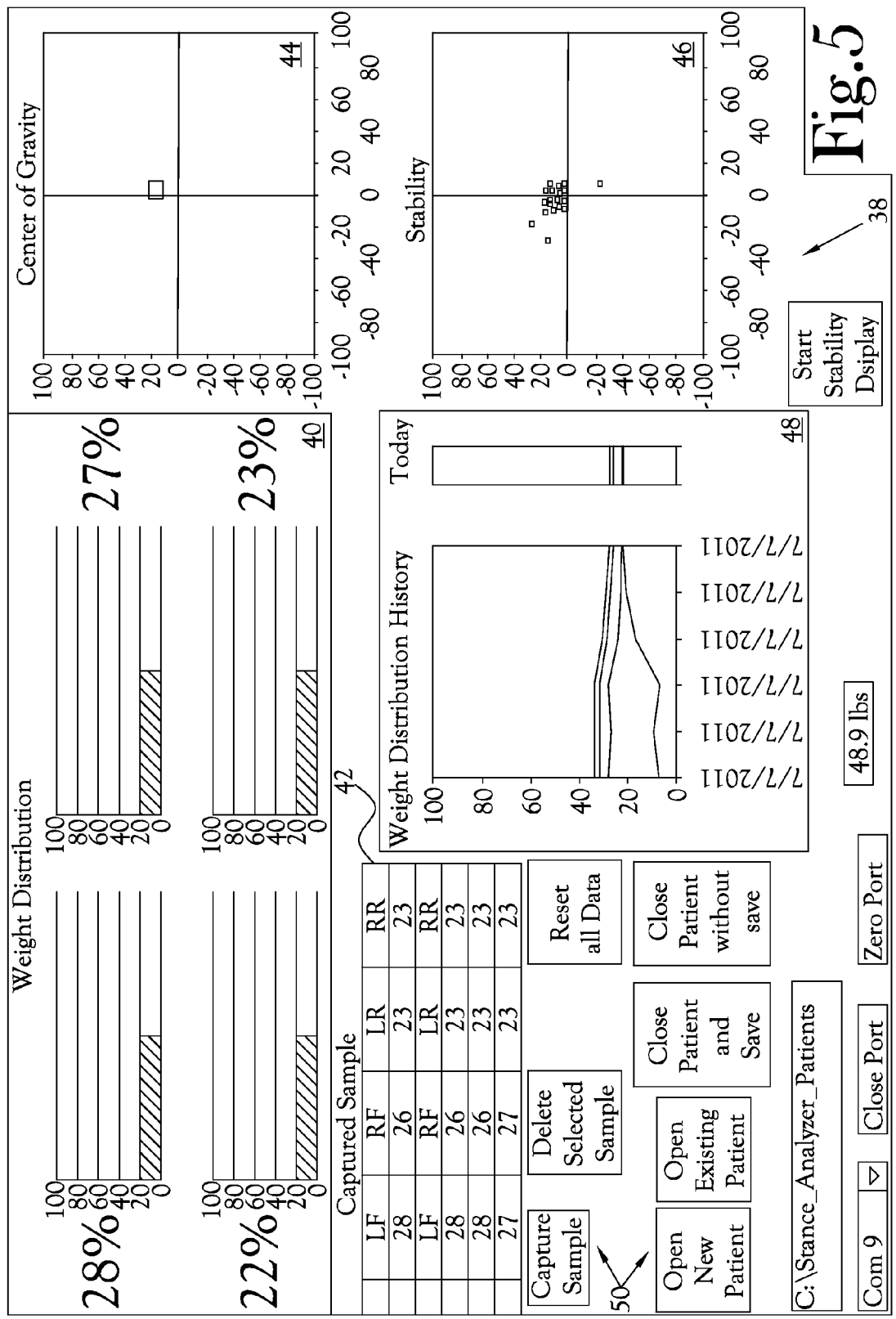
FIG. 5 illustrates a graphic interface generated according to an example embodiment of the present general inventive concept.

FIG. 5 illustrates a graphic interface 38 generated according to an example embodiment of the present general inventive concept. In the illustrated embodiment, the graphic interface 38 provides a plurality of visual representations of weight bearing characteristics of the animal's four legs, wherein the animal started with an injured right-rear leg. As illustrated in FIG. 5, the graphic interface 38 includes an instantaneous view of weight distribution percentages 40 (both in numerical and bar chart format), and a chart 42 including collected, or captured, samples, wherein the larger font numbers on the top row are an average of all the captured samples. Graphical representations of the center of gravity 44 and stability 46 of the animal can be generated, for example, to provide instantaneous and historical views of weight distribution percentages calculated in terms of center-of-gravity and stability, respectively. The graphic interface 38 can include various data controls 50, for example, to open, close, capture, delete, and reset patient data. Furthermore, in some embodiments, sample data points, or snapshots, can be captured through the use of the remote control module 32, wherein the operator can press a button to start/stop the capture of data sets upon observing the animal in a steady state with each paw resting on an associated pressure plate 16, i.e., a quadrant Q1 to Q4, of the stance analyzer 10. For example, the control module can collect the signals from each sensor region over time, and an output signal, or visual representation, can be generated to include a stabilization signal to indicate when the weight applied by each foot is substantially constant over a period of time, based on a comparison of the collected signals. The control unit can include an input unit for a user to periodically start and/or stop the collection of data, remotely or otherwise. The control unit can also be instructed to automatically start and/or stop the collection of data based on a state of the stabilization signal, so that data is only collected when the animal is stably standing on the base member.

As described herein, to help stabilize the animal on the stance analyzer for data collection, an optional food source can be provided proximate one end of the force plate analyzer in order to assist in properly positioning the pet's paws on each force plate. This has been found to keep the animal focused on the food source such that the animal remains stable during data collection.

In the illustrated embodiment, the control unit can include a graphic interface 38. The graphic interface can generate a weight distribution history graph 48 showing a progression of the weight distribution among the animal's various legs over time. It will be recognized that, in many applications of the stance analyzer system 28, one of the goals of animal treatment is to have the percentages of weight distributed among the animal's front legs converge to substantially the same level, over time, and to have the percentages of weight distributed among the animal's hind legs to converge to substantially the same level, over time. Accordingly, the graph 48 showing the progression of weight distribution of the animal may be used to monitor convergence of the weight distribution of the animal, for example, to verify effectiveness of treatment of the animal. For example, in the data set illustrated in the graphic interface 38 of FIG. 5, although the animal started with an injured right-rear leg, through the visualization of tools provided through the graphic interface 38, it can be seen that the animal's right rear leg weight percentage has converged toward the left rear leg percentage over time as is shown in the weight distribution history graph 48. In this embodiment, the weight distribution history graph 48 includes lines representing each leg in order to show the progress of the convergence over time of weight distribution of the animal's injured right rear leg toward the distribution of the animal's left rear leg, thereby demonstrating success of treatment of the animal over time.

The data can be processed to generate an output signal, or visual representation, based on lameness signals indicating lameness of the animal when the weight applied by one foot is substantially less than the weight applied by another foot. This can be achieved by instructing the control unit to generate a lameness signal to indicate lameness of the animal when the weight applied by at least one foot is a predetermined fraction of the weight applied by at least one other foot. The output signal can also include a distribution signal to indicate convergence and/or divergence of the weight applied by at least two different feet, by collecting the data from each foot over time.

Figure 6:
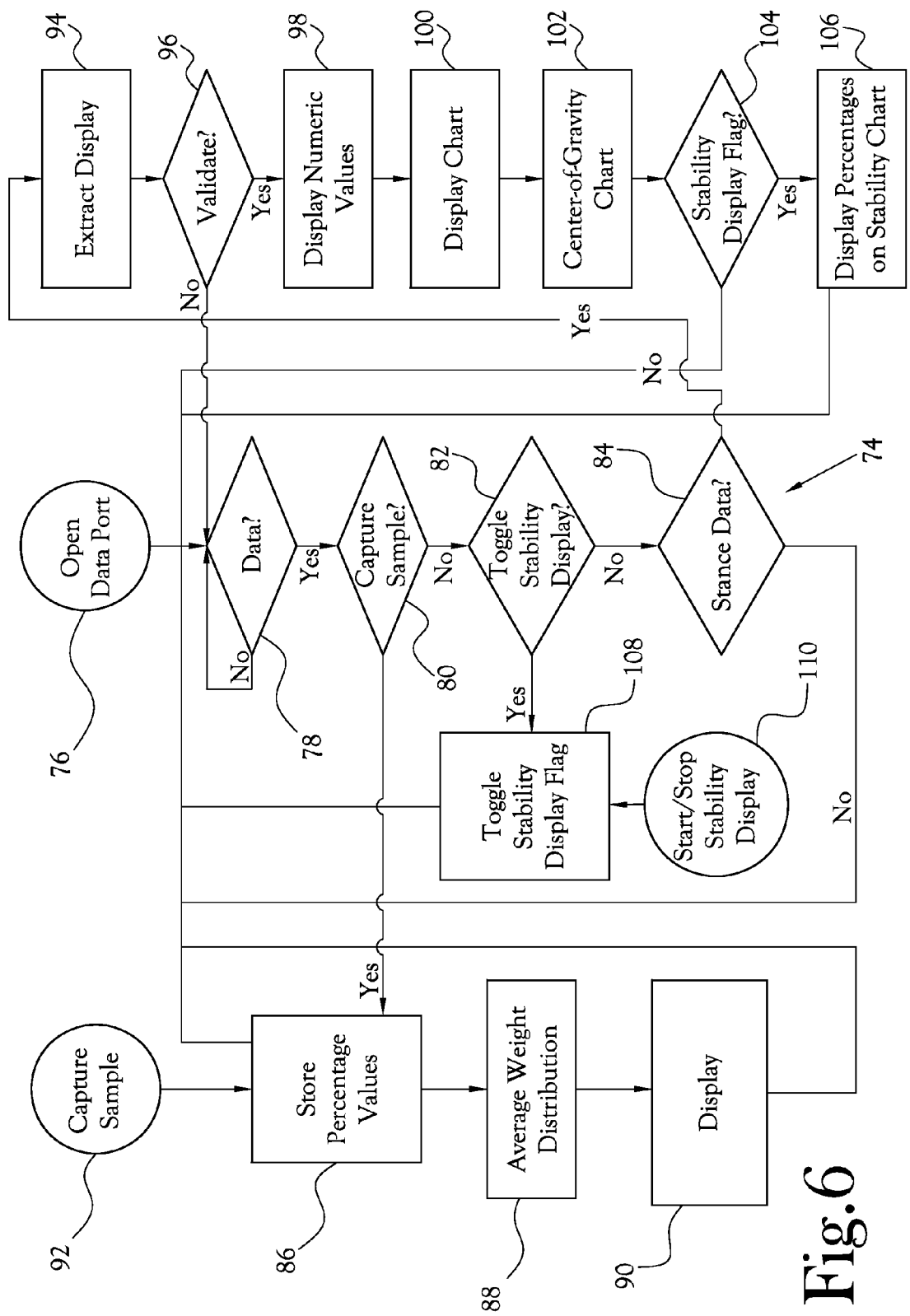
FIG. 6 is a flow chart of a main operational routine performed by circuitry in the control module according to an example embodiment of the present general inventive concept.

FIG. 6 is a flow chart illustrating a main operational routine 74 performed by circuitry in the control module 30 according to an example embodiment of the present general inventive concept. As indicated above, the control module 30 may be a PC or other computer device, and may be configured as integrated unit, or separate, from the stance analyzer 10. Operation of the routine 74 can be selectively controlled via an input unit, e.g., graphic interface 38 and/or remote control module 32. The routine 74 can be repeated and executed as many times as desired to capture sufficient samples of weight distribution data.

An example routine is illustrated in FIG. 6 to carry out various analyses of the present general inventive concept. Referring to FIG. 6, upon initiation of communication 76 between the control module 30 and the stance analyzer 10, the control module 30 performs a determination 78 as to whether data from the stance analyzer 10 is available. If no data is available, the control module 30 repeats the determination 78 as to whether data from the stance analyzer 10 is available until such a time as data is communicated from the stance analyzer 10. In the event data is available, a series of determinations 80, 82, 84 can be made as to whether a weight distribution sample 80 was captured, whether to toggle a stability display flag 82, and whether stance data is being received 84 from the stance analyzer 10. In the event no operating command has been received, the control module 30 repeats the determination 78 as to whether data from the stance analyzer 10 is available, and if data remains available, repeats the series of determinations 80, 82, 84 as to whether an operating command is received, and if so, to determine which type of operating command is received, upon which further actions are performed.

As illustrated in FIG. 6, in the event no operating command to capture a weight distribution sample 80 or to toggle a stability display flag 82 is received, upon receipt of an operating command indicating that stance data is being received 84, the control module 30 extracts 94 a payload of data from the stance analyzer 10. In one embodiment, the data may include indications of measurements of weight distribution percentage values among four legs of an animal standing on the stance analyzer 10, as well as total weight of the animal. A determination 96 is then made as to whether the payload of data is valid. In the event the payload of data is determined not to be valid, the control module 30 repeats the determination 78 as to whether data from the stance analyzer 10 is available, and if data remains available, repeats the series of determinations 80, 82, 84 as to whether another operating command is received. In the event the payload of data is determined to be valid, the four weight distribution percentage values are displayed numerically 98, displayed as values in bar chart format 100, and displayed in a center-of-gravity format 102 on a center-of-gravity chart, on the graphic interface 38. Thereafter, a determination 104 is made as to whether a stability display flag within the main processing loop 74 is turned on. If the stability display flag is turned on, the four weight distribution percentage values are further displayed 106 in a center-of-gravity format on the stability chart of the graphic interface 38, without clearing previous samples from the display. Following the display 106 of the weight distribution percentage values in the center-of-gravity format on the stability chart of the graphic interface 38, the control module 30 repeats the determination 78 as to whether additional data from the stance analyzer 10 is available. If the stability display flag is not turned on, i.e., if it is turned off, the control module 30 repeats the determination 78 as to whether additional data from the stance analyzer 10 is available.

In the illustrated embodiment, upon receipt of an operating command to toggle the stability display flag 82, the stability display flag is toggled 108. More specifically, in the operation of toggling 108 the stability display flag, if the stability display flag is turned on, toggling 108 of the stability display flag results in turning the display flag off. Conversely, if the stability display flag is turned off, toggling 108 of the stability display flag results in turning the display flag on and clearing the Stability Display chart. In the illustrated embodiment, communication of the operating command to toggle the stability display flag 82 may be performed, for example, by inputting the command into the control module 30 via the graphic interface 38, or by pressing a designated "Start/Stop Stability Display" button 110 located on the remote control module 32 or other user interface. Following the operation of toggling 108 the stability display flag, the control module 30 repeats the determination 78 as to whether additional data from the stance analyzer 10 is available.

In the illustrated embodiment, upon receipt of an operating command to capture a weight distribution sample 80, the control module 30 stores 86 the four most recent valid weight distribution percentage values received from the stance analyzer 10, which may correspond, for example, to the most recent measurement of four legs of a four-limbed animal positioned on the stance analyzer 10. The control module 30 then calculates and displays 88 a numerical average of all weight distribution storage array values. The calculated average of all weight distribution storage array values is graphically displayed 90 on a chart on the graphic interface 38, whereupon the control module then repeats the determination 78 as to whether additional data from the stance analyzer 10 is available. In the illustrated embodiment, communication of the operating command to capture a weight distribution sample 80 may be performed, for example, by inputting the command into the control module 30 via the graphic interface 38, or by pressing a designated "Capture Sample" button 92 located on the remote control module 32.

Figure 7:
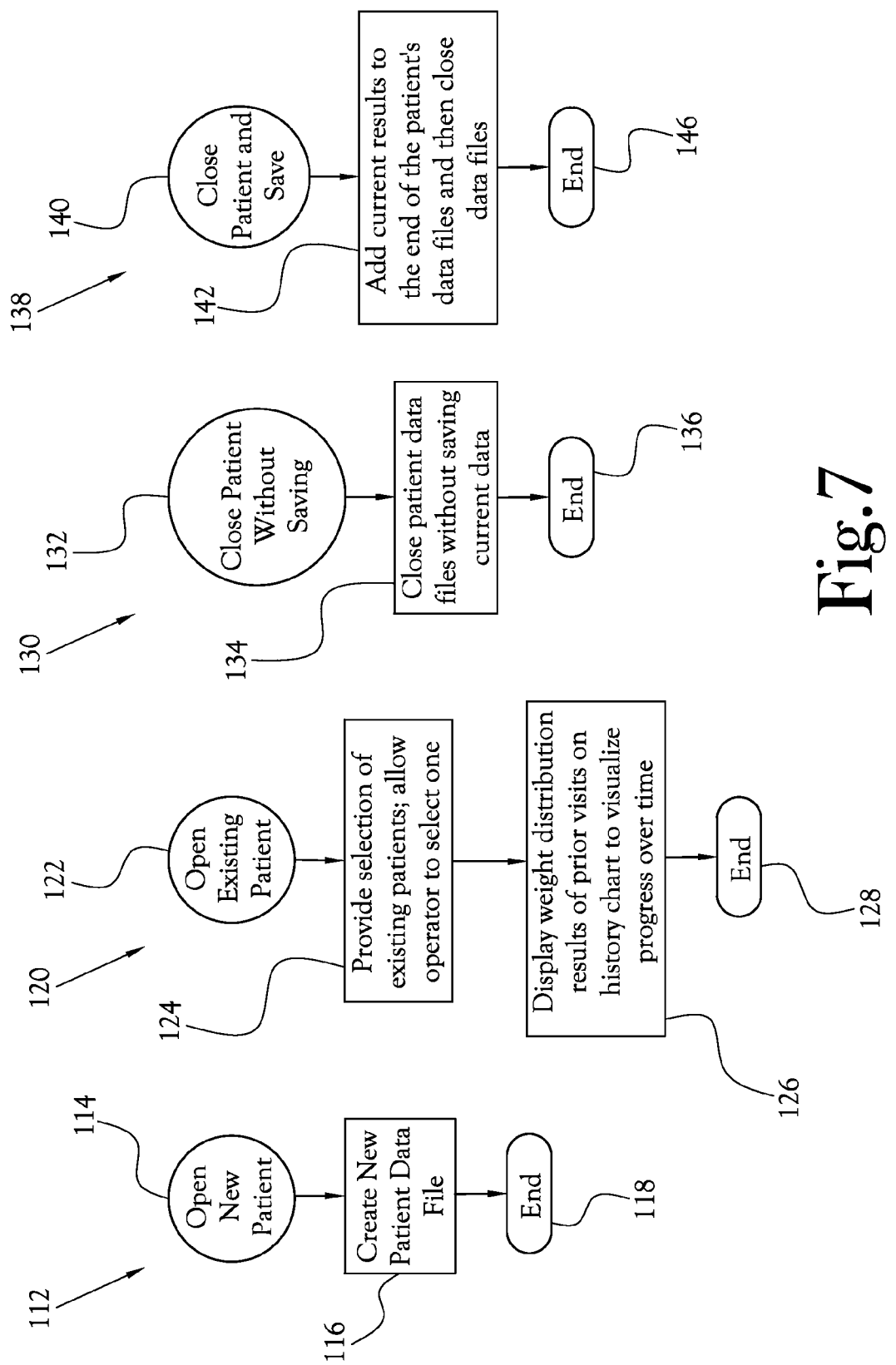
FIG. 7 is a flow chart of patient account routines performed by circuitry in the control module according to an example embodiment of the present general inventive concept.

FIG. 7 is a flow chart showing several patient account routines performed by circuitry in the control module 30 according to an example embodiment of the present general inventive concept. The illustrated routines can be implemented via user interface buttons on the graphic interface 38, or via buttons on the remote control module 32, or other input control. As shown in FIG. 7, in a first patient account routine 112, a first button 114 is provided for opening a new patient account, and upon activating the first button 114, a new patient data file is created 116, whereupon the first patient account routine ends 118. In a second patient account routine 120, a second button 122 is provided for opening an existing patient account. Upon activating the second button 122, a selection of existing patients is displayed 124 on the graphic interface 38, allowing a user to select among one of the displayed existing patient accounts. Upon selection of an existing patient account, the weight distribution results of the prior visits of the patient corresponding to the selected existing patient account can be displayed 126 on a history chart on the graphic interface 38 to allow a user to visualize progress of the patient over time. Thereafter, the second patient account routine ends 128. In a third patient account routine 130, a third button 132 is provided for closing a patient account without saving. Upon activating the third button 132, data files of an opened patient account are closed 134 without saving current data. Thereafter, the third patient account routine ends 136. In a fourth patient account routine 138, a fourth button 140 is provided for closing and saving a patient account. Upon activating the fourth button 140, the current measurement results received from the stance analyzer 10 are added to the patient's data files, and the data files are then closed 142. Thereafter, the fourth patient account routine ends 146.

Figure 8:
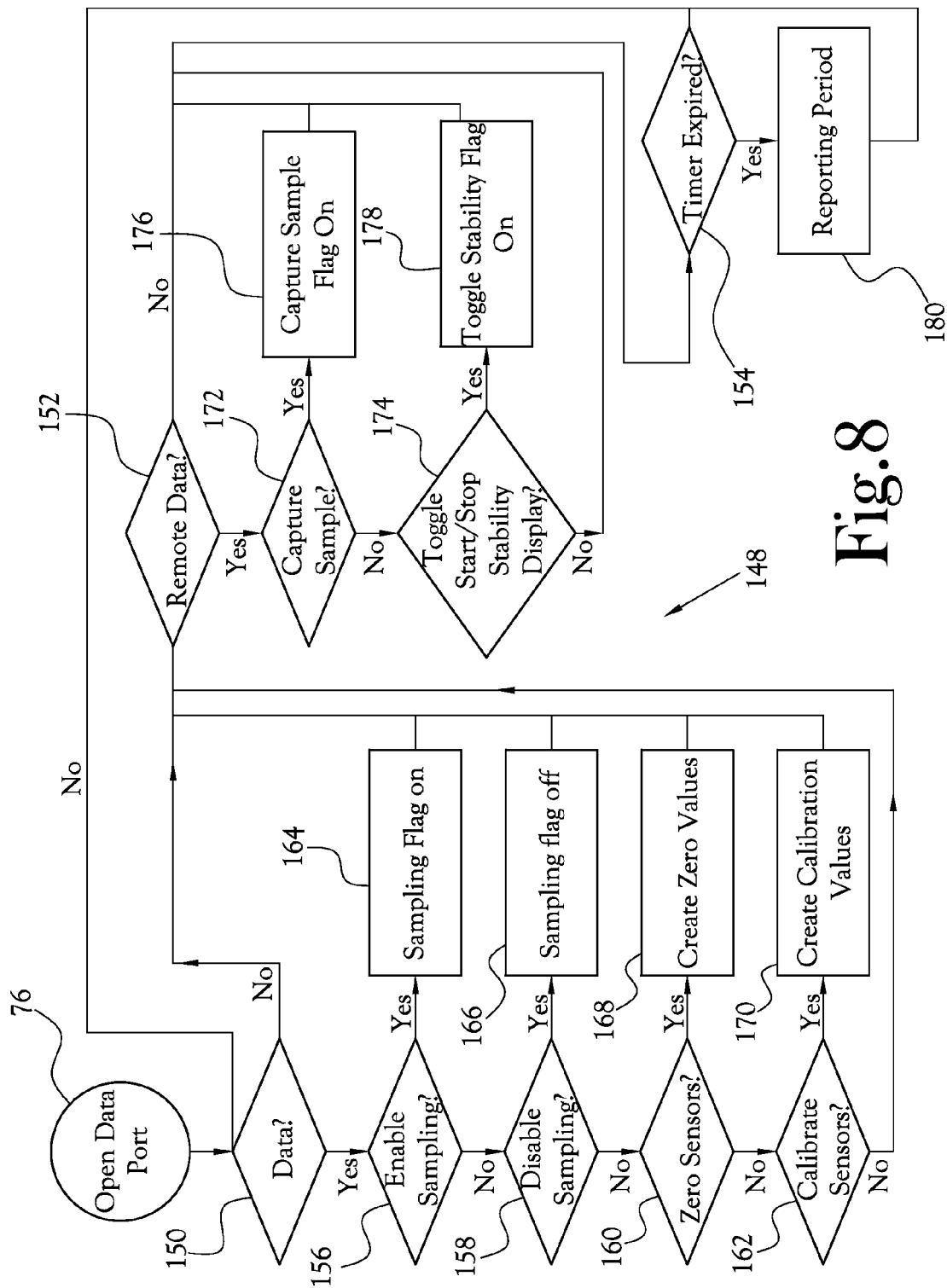
FIG. 8 is a flow chart of a firmware main processing routine performed by circuitry in the stance analyzer module according to an example embodiment of the present general inventive concept.

FIG. 8 is a flow chart of a firmware main processing routine 148 performed by circuitry in the stance analyzer 10 according to an example embodiment of the present general inventive concept. Referring to FIG. 8, in the illustrated embodiment, upon initiation of communication 76 between the control module 30 and the stance analyzer 10, the stance analyzer 10 performs a determination 150 as to whether data from the control module 30 is available. If no data is available, the stance analyzer 10 proceeds to perform a determination 152 as to whether data from the remote control module 32 is available. If no data from the remote control module 32 is available, the stance analyzer 10 proceeds to perform a determination 154 as to whether a reporting period timer has expired. If the reporting period timer has expired, the stance analyzer 10 executes a command 180 to perform a reporting period routine 182. If the reporting period timer has not expired, the stance analyzer 10 repeats the determination 150 as to whether data from the control module 30 is available, until such a time as data from either the control module 30 or the remote control module 32 is available, or until such a time as the reporting period timer has expired.

In the event the determination 150 as to whether data from the control module 30 is available indicates that data from the control module 30 is available, a series of determinations 156, 158, 160, 162 are made as to whether one of a number of operating commands is received. For example, an operating command to disable sampling 158, an operating command 160 to zero the sensors of the stance analyzer 10, and an operating command 162 to calibrate the sensors of the stance analyzer 10. In the event the available data from the control module 30 does not correspond to one of these operating commands, the stance analyzer 10 proceeds to perform the determination 152 as to whether data from the remote control module 32 is available. In the event the available data from the control module 30 does correspond to one of the above-discussed operating commands, the determinations 156, 158, 160, 162 determine which type of operating command is received, upon which further action is performed by the stance analyzer 10 before proceeding to perform the determination 152 as to whether data from the remote control module 32 is available. For example, in the event the data from the control module 30 is determined 156 to correspond to the operating command to enable sampling, a sampling flag is turned on 164. Conversely, in the event the data from the control module 30 is determined 158 to correspond to the operating command to disable sampling, the sampling flag is turned off 166. In the event the data from the control module 30 is determined 160 to correspond to the operating command to zero the sensors of the stance analyzer 10, the sensors of the stance analyzer 10 are sampled a number of times, and the readings from the sensors are used to establish zero values 168 of the readings from the sensors. In the event the data from the control module 30 is determined 162 to correspond to the operating command to calibrate the sensors of the stance analyzer 10, the sensors of the stance analyzer 10 are sampled a number of times, and the readings from the sensors are used to establish calibration values 170 corresponding to a calibration weight applied to the sensors. Following performance of the appropriate action corresponding to the appropriate determination 156, 158, 160, 162 as to which type of operating command is received, the stance analyzer 10 proceeds to perform the determination 152 as to whether data from the remote control module 32 is available.

In the event the determination 152 as to whether data from the remote control module 32 is available indicates that data from the remote control module 32 is available, a series of additional determinations 172, 174, are made as to whether one of a number of additional operating commands is received. For example, an operating command to capture a sample 172, and an operating command to toggle start/stop stability display 174. In the event the available data from the remote control module 32 does not correspond to one of these additional operating commands, the stance analyzer 10 proceeds to perform the determination 154 as to whether the reporting period timer has expired. In the event the available data from the remote control module 32 does correspond to one of the above-discussed additional operating commands, the determinations 172, 174 determine which type of additional operating command is received, upon which further action is performed by the stance analyzer 10 before proceeding to perform the determination 154 as to whether the reporting period timer has expired. For example, in the event the data from the remote control module 32 is determined 172 to correspond to the operating command to capture a sample, a capture sample flag is turned on 176. In the event the data from the remote control module 32 is determined 174 to correspond to the operating command to toggle start/stop stability display, a toggle stability flag is turned on 178. Following performance of the appropriate action corresponding to the appropriate determination 172, 174 as to which type of additional operating command is received, the stance analyzer 10 proceeds to perform the determination 154 as to whether the reporting period timer has expired.

Figure 9:
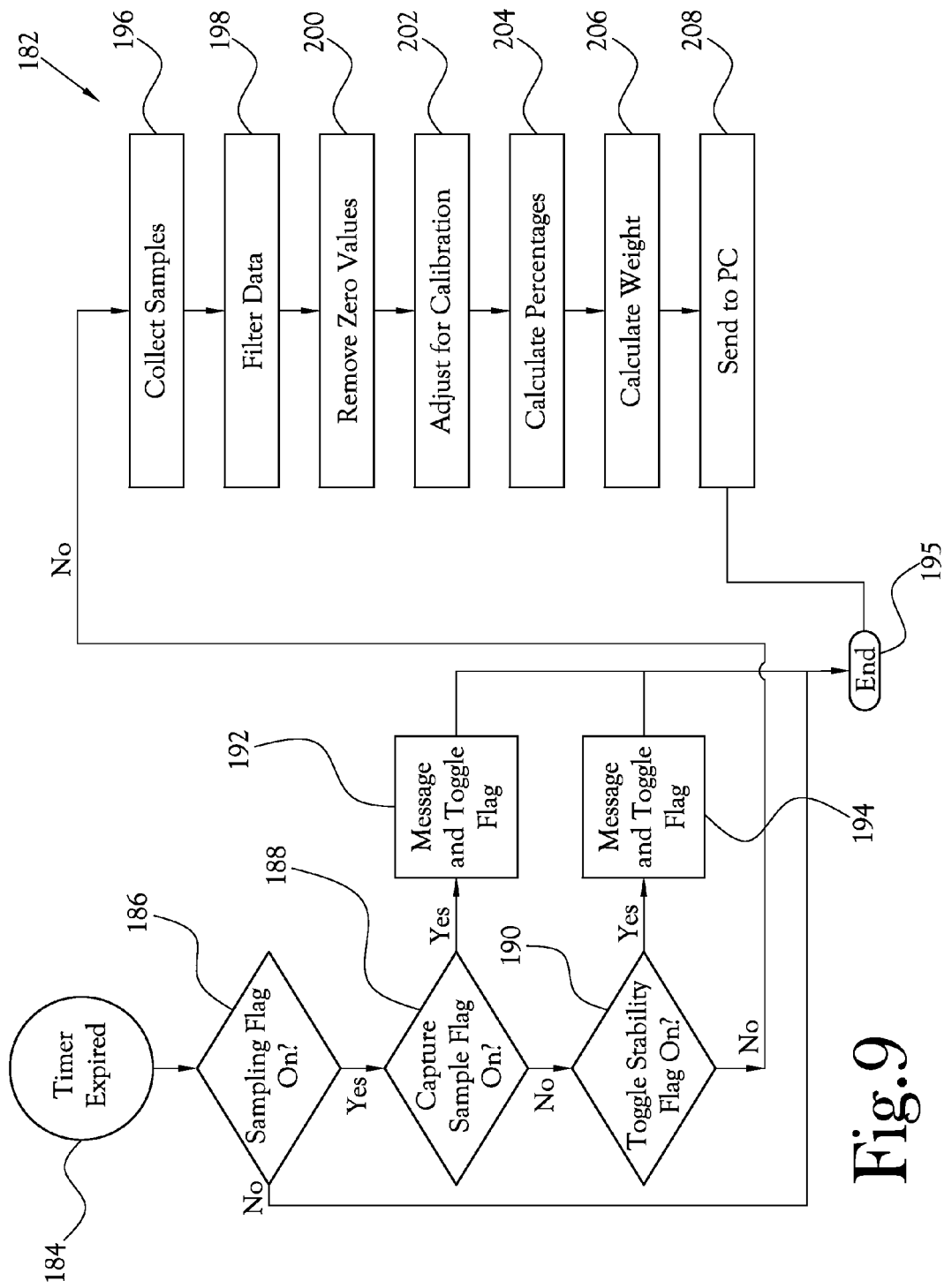
FIG. 9 is a flow chart of a firmware reporting period routine performed by circuitry in the stance analyzer module according to an example embodiment of the present general inventive concept.

FIG. 9 is a flow chart of a firmware reporting period routine 182 performed by circuitry in the stance analyzer 10 according to an example embodiment of the present general inventive concept. As illustrated in FIG. 9, upon a determination 154 that the reporting period timer of the stance analyzer 10 has expired 184, the reporting period routine 182 is initiated. At the onset of the reporting period routine 182, a series of determinations 186, 188, 190 are made as to whether one of a number of conditions of the circuitry of the stance analyzer 10 is met, and upon confirmation that any of the conditions of the circuitry of the stance analyzer 10 is met, additional actions are taken by the circuitry in the stance analyzer 10. For example, in the illustrated embodiment, following the determination 154 that the reporting period timer of the stance analyzer 10 has expired 184, a determination 186 is made as to whether the sampling flag of the stance analyzer 10 is on. In the event the sampling flag is not on, the reporting period routine 182 ends 196. In the event the sampling flag is on, an additional determination 188 is made as to whether the capture sample flag is on. In the event the capture sample flag is on, a message is sent to the control module 30 to capture a sample and the capture sample flag is turned off 192, whereupon the reporting period routine 182 ends 196. In the event the capture sample flag is off, an additional determination 190 is made as to whether the toggle stability flag is on. In the event the toggle stability flag is on, a message is sent to the control module 30 to toggle the stability and the toggle stability flag is turned off 194, whereupon the reporting period routine 182 ends 195.

In the event the sampling flag is determined 186 to be off, the capture sample flag is determined 188 to be off, and the toggle stability flag is determined 190 to be off, sample data is collected 196 from each sensor. The sample data is filtered 198 and any "zero" values are removed 200 from the filtered data. The filtered data is then adjusted 202 to account for the various calibration values of the specific sensors. Thereafter, the data is analyzed to calculate the total weight applied to all sensors 206 and the percentages of load 204 distributed per sensor. The total weight value and the percentage values are then sent 208 to the control module 30 for further analysis and use, such as for example for display on the graphic interface 38. Thereafter, the reporting period routine 182 ends 195.

Figure 10:
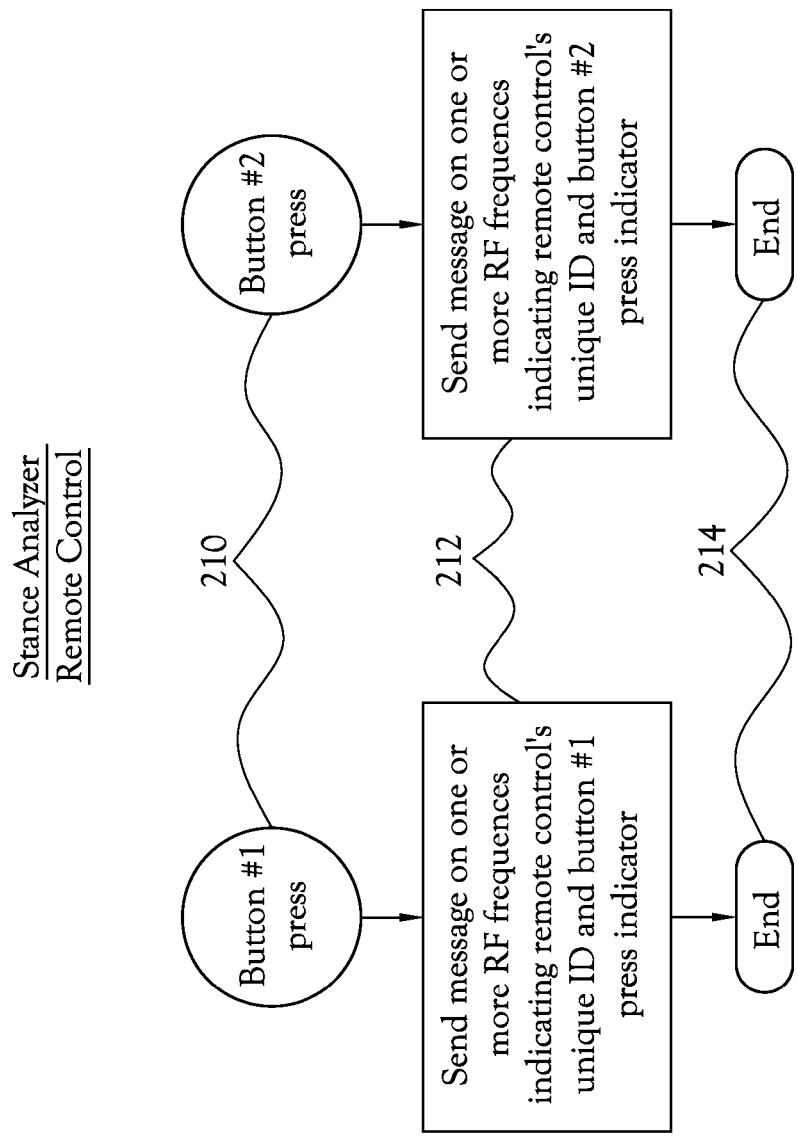
FIG. 10 is a flow chart of routines performed by circuitry in the remote control module according to an example embodiment of the present general inventive concept.

FIG. 10 is a flow chart showing various routines performed by circuitry in the remote control module 32 according to an example embodiment of the present general inventive concept. As illustrated in FIG. 10, when a button on the remote control module 32 is pressed 210, a message is sent 212 indicating a unique identifier of the pressed button by the remote control module 32. For example, in certain embodiments, the message may be one or more radio frequency signals. Thereafter, the routine of the remote control module 32 ends 214.

In some embodiments, the example stance analyzer system 28 can be used in combination with other pet pain management and rehabilitation devices to provide safe and efficacious therapy that reduces pain and enhances wound healing. For example, the system 28 can be used in combination with electrotherapy, ultrasound, and laser-based equipment to identify targeted areas of the animal in order to increase the efficacy of such treatments. The system 28 can be integrated with several different modalities of treatment, or combinations thereof, to target specific areas of the animal based on the results of the stance analyzer measurements to improve discovery and treatment of ailments to promote better healing. The system 28 can monitor improvement and provide validation of physical rehabilitation over time. The system 28 objectively observes subtle lameness that animals often disguise, eliminating subjective interpretations, and aids in potentially locating additional issues that may have been overshadowed by an obvious lameness in another area. The pet owner is able to observe the pet's progress while reinforcing the benefits of a prescribed treatment program.

Example embodiments of the present general inventive concept can also be achieved by providing a stance analyzer system for use by veterinarians and/or pet owners to objectively diagnose lameness in four legged animals, such as but not limited to dogs, and to further determine which legs are affected. In some embodiments, the stance analyzer is designed to include four force plates positioned such that a pet, such as a dog, stands with each paw on a separate plate. The weight distribution of the pet on each paw can be determined and analyzed. Data collected from the stance analyzer sensors can be fed into a computer. The computer can be programmed to calculate certain body weight distribution characteristics and to convert that information into selected displays and vectors providing ready data for understanding and tracking corrective treatment of the pet.

Analysis of the information can be easily accessed by a technician by means of remote control. The computer can be programmed to include a graphic interface that allows a quick visual of the pet's stance and stability. A food source can be provided proximate one end of the force plate analyzer in order to assist in properly positioning the pet, such that the animal is focused on the food source and remains stable during data collection. The device can include a gimbal system to exaggerate the pet's reaction to stance distribution characteristics.

The present general inventive concept can also be embodied as computer-readable codes on a computer-readable medium. The computer-readable medium can include a computer-readable recording medium and a computer-readable transmission medium. The computer-readable recording medium is any data storage device that can store data as a program which can be thereafter read by a computer system. Examples of the computer-readable recording medium include read-only memory (ROM), random-access memory (RAM), CD-ROMs, DVDs, magnetic tapes, floppy disks, flash memory, and optical data storage devices. The computer-readable recording medium can also be distributed over network coupled computer systems so that the computer-readable code is stored and executed in a distributed fashion. The computer-readable transmission medium can transmit carrier waves or signals (e.g., wired or wireless data transmission through the Internet). Also, functional programs, codes, and code segments to accomplish the present general inventive concept can be easily construed by programmers skilled in the art to which the present general inventive concept pertains.

It is noted that numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Accordingly, while the present general inventive concept has been illustrated by description of several example embodiments, it is not the intention of the applicant to restrict or in any way limit the scope of the inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings.

The invention claimed is:

1. A system to analyze the distribution of weight of an animal, comprising:
    a base member;
    a plurality of sensor regions connected to the base member to respectively receive feet of the animal when the animal is standing, each sensor region having a plurality of sensors to generate signals indicative of weight applied by each foot to a respective sensor region, at least a portion of the sensors being located between the base member and the sensor regions and spaced apart proximate perimeter portions of each sensor region; and
    a control unit to generate an output indicative of the weight applied by each foot to the respective sensor regions based on an aggregation of the generated signals.

2. The system of claim 1, wherein the control unit collects the signals from each sensor region over time.

3. The system of claim 2, wherein the output includes a stabilization signal to indicate when the weight applied by each foot is substantially constant over a period of time, based on a comparison of the collected signals.

4. The system of claim 2, wherein the control unit includes an input unit for a user to periodically start and/or stop the collection of data.

5. The system of claim 3, wherein the control unit automatically starts and/or stops the collection of data based on a state of the stabilization signal.

6. The system of claim 1, wherein the output includes a lameness signal to indicate lameness of the animal when the weight applied by at least one foot is a predetermined fraction of the weight applied by at least one other foot.

7. The system of claim 1, wherein the output signal includes a distribution signal to indicate convergence and/or divergence of the weight applied by at least two different feet over time.

8. The system of claim 1, further comprising a food source holder to hold a food source proximate the animal's mouth when the animal is standing on the base member.

9. The system of claim 1, further comprising a fence member to stabilize the animal when the animal is standing on the base member.

10. The system of claim 1, wherein the position of the animal's feet relative to each respective sensor region does not substantially change the generated signals.

11. The system of claim 1, further comprising a gimbal system to adjust a position and/or level of the base member.

12. The system of claim 1, wherein the plurality of sensor regions are respectively defined by one or more corresponding pressure plates having a first surface to receive the animal's feet and a second surface opposite the first surface and facing the base member to contact the plurality of sensors, the pressure plates being substantially rectangularly shaped such that the at least a portion of the sensors are located proximate four corners of the pressure plates.

13. A method of analyzing the distribution of weight of an animal, comprising:
    providing a base member having a plurality of sensor regions on which the animal stands;
    locating each foot of the animal on a respective sensor region;
    generating signals indicative of weight applied by each foot to the respective sensor regions from a plurality of sensors, wherein at least a portion of the sensors are located between the base member and the sensor regions and are spaced apart proximate perimeter portions of each sensor region; and
    generating an output indicative of the weight applied by each foot to the respective sensor regions, based on an aggregation of the generated signals.

14. The method of claim 13, further comprising collecting the signals from each sensor region over time.

15. The method of claim 14, wherein the output includes a stabilization signal to indicate when the weight applied by each foot is substantially constant over a period of time, based on a comparison of the collected signals.

16. The method of claim 15, further comprising periodically starting and/or stopping the collection of data based on a state of the stabilization signal.

17. The method of claim 13, wherein the output includes a lameness signal to indicate lameness of the animal when the weight applied by at least one foot is a predetermined fraction of the weight applied by at least one other foot.

18. The method of claim 13, wherein the output includes a distribution signal to indicate convergence and/or divergence of the weight applied by at least two different feet over time.

19. The method of claim 13, further comprising adjusting a position and/or level of the base member while the animal is standing on the base member.

20. The method of claim 13, further comprising feeding the animal while the animal's feet are located on the respective sensor regions.

21. A system to analyze the distribution of weight of an animal, comprising:
    a base member;
    four sensor regions, each having a respective pressure plate connected to the base member to respectively receive a foot of the animal when the animal is standing, such that each foot is standing on a different pressure plate and each sensor region having a plurality of sensors located proximate a perimeter of each pressure plate to generate signals indicative of weight applied by each foot to the respective pressure plate; and
    a control unit to generate an output indicative of the weight applied by each foot to the respective pressure plate based on an aggregation of the generated signals from each sensor.

22. The system of claim 21, wherein each sensor comprises a first and second spacer and a pressure transducer, the first spacer being configured to separate the pressure transducer from the base member and to provide a bearing surface for the pressure transducer against the base member, and the second spacer being configured to separate the pressure transducer from the respective pressure plate and to provide a bearing surface for the respective pressure plate to bear against a corresponding pressure transducer.

23. The system of claim 21, wherein the sensor region includes a mat connected to a top surface of each pressure plate.

24. The system of claim 21, further comprising a display device to receive the output of the control unit via wired or wireless transmission and to display a visual representation of the output.

25. The system of claim 24, wherein the display device is a computer or other wireless device.

26. The system of claim 21, further comprising a remote control to periodically start and/or stop the collection of data.

* * * * *